(12) United States Patent
Yamamoto et al.

(10) Patent No.: US 9,180,313 B2
(45) Date of Patent: Nov. 10, 2015

(54) RANGE SHIFTER AND PARTICLE RADIOTHERAPY DEVICE

(75) Inventors: Hirohide Yamamoto, Chiyoda-ku (JP); Takeshi Hagino, Chiyoda-ku (JP); Hiromitsu Inoue, Chiyoda-ku (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 14/375,863

(22) PCT Filed: Feb. 22, 2012

(86) PCT No.: PCT/JP2012/054201
§ 371 (c)(1),
(2), (4) Date: Jul. 31, 2014

(87) PCT Pub. No.: WO2013/124975
PCT Pub. Date: Aug. 29, 2013

(65) Prior Publication Data
US 2015/0031933 A1    Jan. 29, 2015

(51) Int. Cl.
*G21K 5/04* (2006.01)
*A61N 5/10* (2006.01)
*G21K 1/10* (2006.01)

(52) U.S. Cl.
CPC ............ *A61N 5/1048* (2013.01); *A61N 5/1043* (2013.01); *A61N 5/1079* (2013.01); *G21K 1/10* (2013.01); *A61N 2005/1087* (2013.01); *A61N 2005/1095* (2013.01)

(58) Field of Classification Search
USPC ............ 250/396 R, 397, 492.1, 492.3, 505.1, 250/515.1; 600/1
See application file for complete search history.

(56) References Cited

U.S. PATENT DOCUMENTS

2009/0008575 A1* 1/2009 Okazaki et al. ............ 250/492.1
2011/0101235 A1  5/2011 Iwata
(Continued)

FOREIGN PATENT DOCUMENTS

JP    10-127792 A    5/1998
JP    10-314323 A    12/1998
(Continued)

OTHER PUBLICATIONS

International Search Report (PCT/ISA/210) mailed on Mar. 19, 2012, by the Japanese Patent Office as the International Searching Authority for International Application No. PCT/JP2012/054201.
(Continued)

*Primary Examiner* — Nicole Ippolito
(74) *Attorney, Agent, or Firm* — Buchanan Ingersoll & Rooney PC

(57) ABSTRACT

There is provided a range shifter which includes a transmissive plate whose thickness has been adjusted depending on a setup value of an amount of energy to be attenuated, and a holder portion that holds the transmissive plate, wherein the thickness of the transmissive plate is adjusted to be a thickness equivalent to an attenuation amount lower than the setup value by a predetermined rate thereof; and wherein, a superimposing mechanism capable of releasably superimposing an adjustment sheet over the transmissive plate, is provided to at least one of the transmissive plate and the holder portion, the adjustment sheet being adjusted to have a thickness equal to or less than a thickness equivalent to a two-fold attenuation amount of the predetermined rate.

8 Claims, 4 Drawing Sheets

(56) References Cited

U.S. PATENT DOCUMENTS

| | | | |
|---|---|---|---|
| 2012/0108958 A1* | 5/2012 | Jackson | ........................ 600/427 |
| 2013/0253252 A1 | 9/2013 | Iwata | |

FOREIGN PATENT DOCUMENTS

| | | |
|---|---|---|
| JP | 11-262538 A | 9/1999 |
| JP | 2001-212253 A | 8/2001 |
| JP | 2006-34582 A | 2/2006 |
| JP | 2007-307223 A | 11/2007 |
| JP | 2008-194441 A | 8/2008 |
| JP | 2010-32419 A | 2/2010 |
| JP | 2010-148833 A | 7/2010 |
| JP | 2010-175309 A | 8/2010 |
| JP | 2010-187900 A | 9/2010 |
| TW | 201116316 A1 | 5/2011 |

OTHER PUBLICATIONS

Japanese Office Action dated Jan. 27, 2015 issued in corresponding Japanese Patent Appln. No. 2014-500787, with English translation (6 pages).

Office Action issued on Aug. 6, 2014, by the Taiwanese Patnet Office in counterpart Taiwanese Patent Application No. 101120230, and an English translation of the Office Action. (8 pages).

Japanese Decision of Refusal issued by the Japanese Patent Office on Jul. 14, 2015 in corresponding JP Application No. 2014-500787, with full English translation (4 pages).

* cited by examiner

RANGE SHIFTER AND PARTICLE RADIOTHERAPY DEVICE

TECHNICAL FIELD

The present invention relates to a particle beam therapy system for performing a treatment through irradiation with a particle beam, and in particular, to a range shifter for adjusting a range of the particle beam.

BACKGROUND ART

A particle beam therapy, which is a treatment of a deceased tissue by irradiating it with a particle beam to thereby damage the tissue, is a part of broad-sense radiation therapy. However, unlike a y-ray, an X-ray or like other ray, the imparted dose of a particle beam such as a proton beam, a heavy ion beam, etc., becomes maximum abruptly in a specific depth range (Bragg peak) in a body according to energy of the particle beam. Thus, in the particle beam therapy, it is possible to control the irradiation region (irradiation field), not only as a planar shape, but also in a depth direction by adjusting the energy.

Meanwhile, since the facility of an accelerator that is a beam source for the particle beam therapy is huge, the particle beam emitted from a single beam source is distributed to a plurality of treatment rooms, individually. Although the energy of the particle beam is adjustable by changing the condition of the accelerator, it takes time. Thus, what is generally taken is to provide a device having a transmissive plate of a predetermined thickness, so-called "range shifter", in each of the treatment rooms, to thereby adjust the energy of the particle beam according to its attenuation amount during transmission in the transmissive plate (see, for example, Patent Documents 1 to 9).

CITATION LIST

Patent Document

Patent Document 1: Japanese Patent Application Laid-open No. H10-314323 (paragraph 0016, FIG. 21(a) to (d))
Patent Document 2: Japanese Patent Application Laid-open No. H11-262538 (paragraphs 0004 to 0005, FIG. 11)
Patent Document 3: Japanese Patent Application Laid-open No. 2001-212253 (paragraph 0119, FIG. 7; paragraphs 0141 to 0147, FIG. 9)
Patent Document 4: Japanese Patent Application Laid-open No. 2006-034582 (paragraphs 0037 to 0038, FIG. 10)
Patent Document 5: Japanese Patent Application Laid-open No. 2007-307223 (paragraph 0017, FIG. 3)
Patent Document 6: Japanese Patent Application Laid-open No. 2010-032419 (paragraph 0035, FIG. 1)
Patent Document 7: Japanese Patent Application Laid-open No. 2010-148833 (paragraphs 0028 to 0057, FIG. 2 to FIG. 6)
Patent Document 8: Japanese Patent Application Laid-open No. 2010-175309 (paragraphs 0019 to 0020, 0024, FIG. 2, FIG. 3)
Patent Document 9: Japanese Patent Application Laid-open No. 2010-187900 (paragraphs 0033 to 0037, FIG. 1)

SUMMARY OF THE INVENTION

Problems to be Solved by the Invention

However, these technologies disclosed are intended to adjust a water-equivalent thickness, for example, as the attenuation amount equivalent to an in-body depth, by selecting the material or the thickness of the transmissive plate. Nevertheless, the attenuation amount at the time the particle beam transmits through the transmissive plate, i.e. an actual water-equivalent thickness, is not always constant depending on the condition of the transmitting particle beam. Thus, even when a range shifter is used which has, for example, the transmissive plate whose material and thickness have been finished exactly as specified, there is a possibility that a difference in the water-equivalent thickness occurs depending on what the treatment room is, or occurs even in the same treatment room, if its condition has changed by the maintenance or the like.

This invention has been made to solve the problem as described above, and an object thereof is to provide a range shifter and a particle beam therapy system which can adjust a range of the particle beam exactly as specified,

Means for Solving the Problems

The range shifter of the invention is a range shifter that outputs a particle beam incident thereto while attenuating energy of the particle beam, characterized by comprising a transmissive plate whose thickness has been adjusted depending on a setup value of an amount of the energy to be attenuated, and a holder portion that holds the transmissive plate, wherein the thickness of the transmissive plate is adjusted to be a thickness equivalent to an attenuation amount lower than the setup value by a predetermined rate thereof, and wherein a superimposing mechanism capable of releasably superimposing an adjustment sheet over the transmissive plate, is provided to at least one of the transmissive plate and the holder portion, said adjustment sheet being adjusted to have a thickness equal to or less than a thickness equivalent to a two-fold attenuation amount of the predetermined rate.

Effect of the Invention

According to the range shifter of the invention, even when its attenuation amount of the energy changes due to a change in the condition of the incident particle beam, it is possible to make adjustment to the setup attenuation amount of the energy by superimposing the adjustment sheet whose thickness can be adjusted. Thus, it is possible to achieve a range shifter that adjusts the range of the particle beam accurately, and a particle beam therapy system that can make irradiation with an accurate irradiation field.

MODES FOR CARRYING OUT THE INVENTION

Embodiment 1

Hereinafter, a configuration of a range shifter according to Embodiment 1 of the invention and a method of adjusting the same, will be described. FIG. 1 to FIG. 4 are for illustrating the range shifter and its adjusting method according to Embodiment 1 of the invention, in which shown at FIG. 1(a) and FIG. 1(b) are a top view (a) showing the configuration of the range shifter, and cross-sectional views (b) taken along line I-I in the top view, individually showing transmissive units of typical three types that are different depending on a thickness of the transmissive plate.

Figure 2:
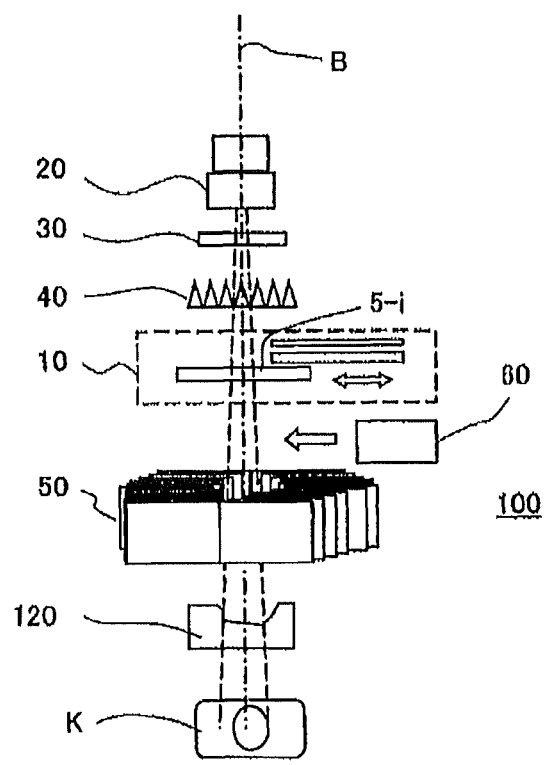
FIG. 2 is a diagram showing a configuration of an irradiation device provided with the range shifter according to Embodiment 1 of the invention.
Figure 3:
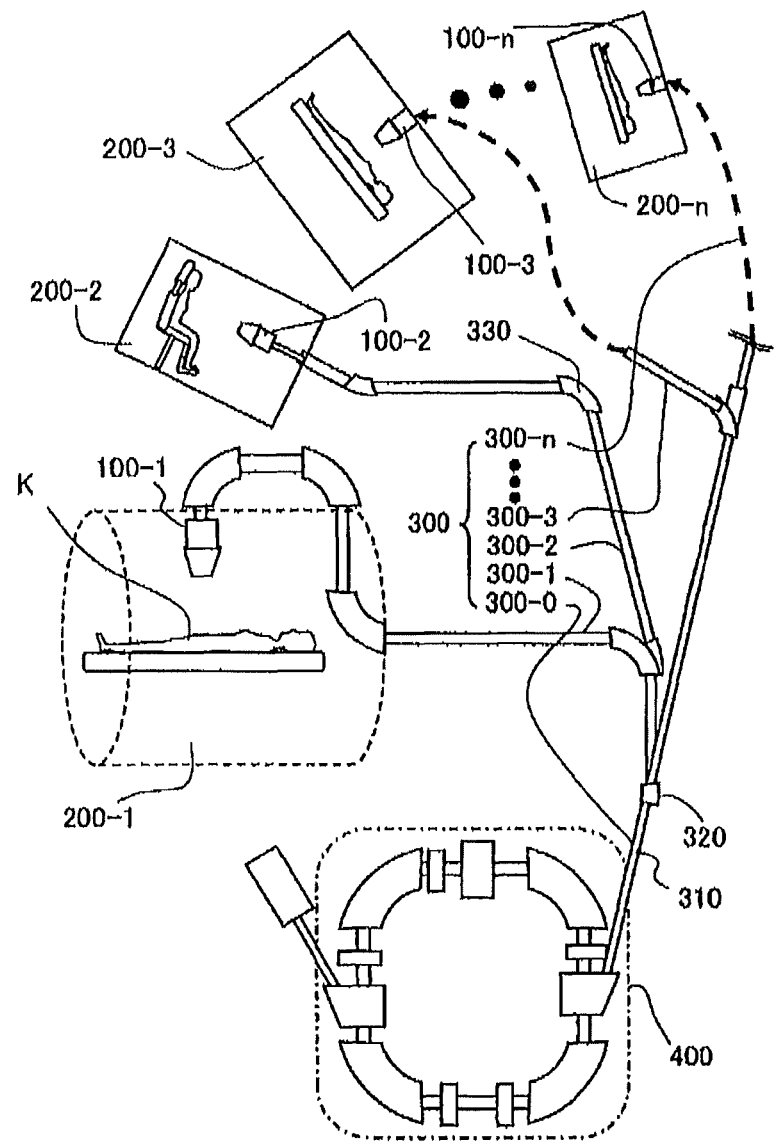
FIG. 3 is a diagram showing a configuration of a particle beam therapy system according to Embodiment 1 of the invention.
Figure 4:
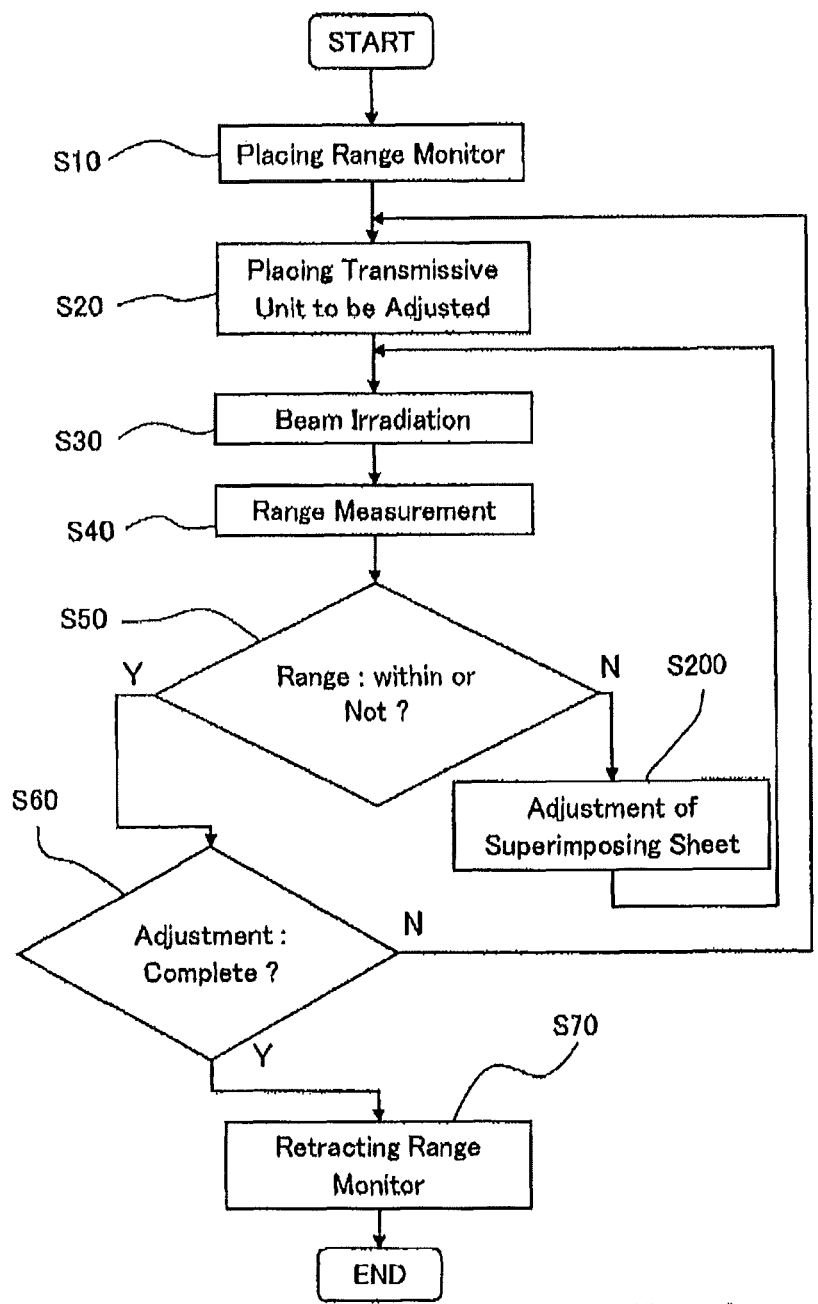
FIG. 4 is a flowchart for illustrating a method of adjusting the range shifter according to Embodiment 1 of the invention.

Meanwhile, FIG. 2 is a schematic diagram showing a configuration of an irradiation device provided with the range shifter according to Embodiment 1 of the invention. FIG. 3 is a diagram showing a configuration of a particle beam therapy system provided with the aforementioned irradiation device in each treatment room. Further, FIG. 4 is a flowchart for illustrating a method of adjusting the range shifter according to Embodiment 1 of the invention, at the time the irradiation device provided with the range shifter is installed or subjected to its maintenance.

Figure 1A:
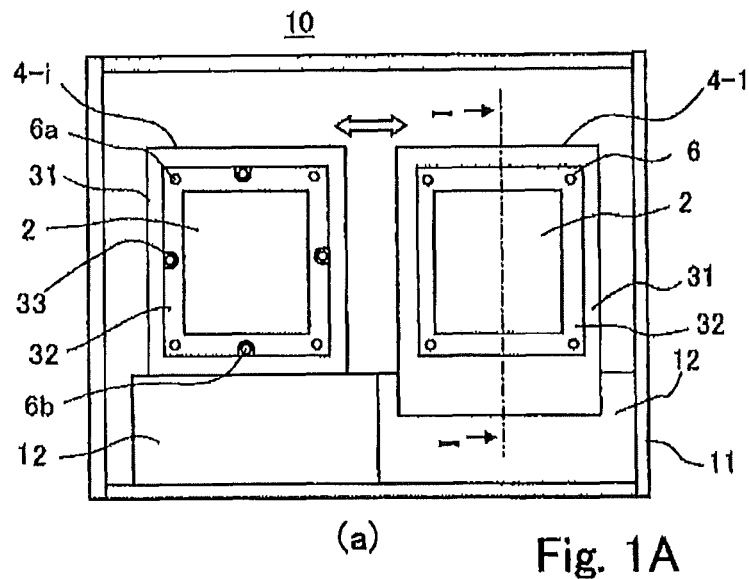
FIG. 1A and FIG. 1B are a top view for illustrating a configuration of a range shifter according to Embodiment 1 of the invention, and cross-sectional views showing configurations of holder portions of different thickness-dependent types.
Figure 1B:
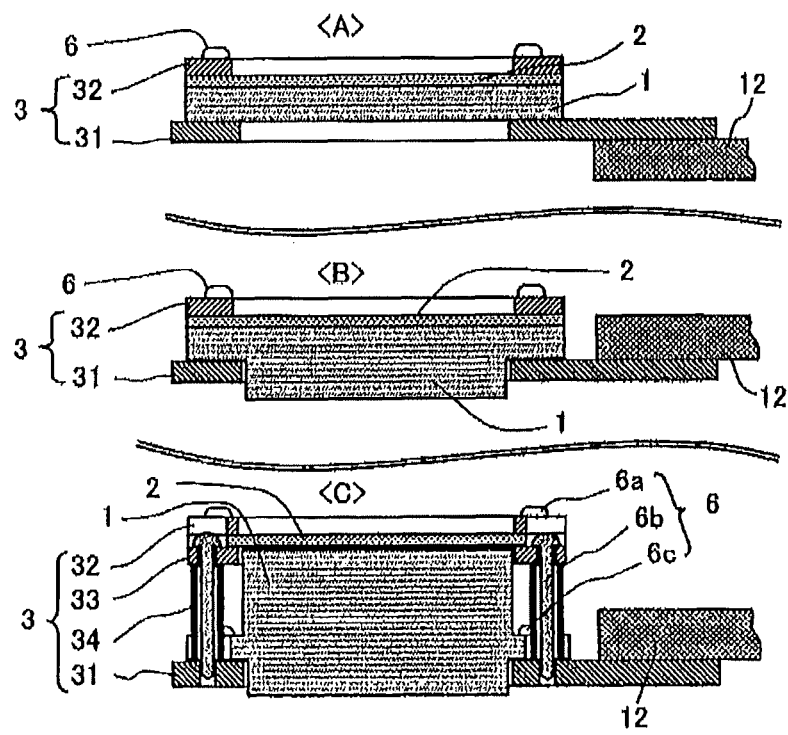

As shown in FIG. 1(a), the range shifter 10 includes a plurality of transmissive units 4 in a housing 11, each provided with a transmissive plate 1 in a manner allowing it to enter into or leave from an irradiation region of the particle beam. As shown in FIG. 1(b), the plurality of transmissive units 4 include the transmissive plates 1 having different thicknesses according to their respective setup attenuation amounts of the particle beam energy, and a frame 3 holding the transmissive plate 1 is connected by way of a driving cylinder 12 to the housing 11, so that it is possible to cause the transmissive plate 1 to move between a retracted position and an irradiation position. What is a feature of this invention is that each of the transmissive units 4 is configured in such a manner that an adjustment sheet 2 capable of adjusting thickness can be superimposed releasably over the transmissive plate 1 in order to adjust the attenuation amount.

The transmissive plate 1 is formed of a polyethylene plate in which at least a region where the particle beam transmits (for example, a 200-mm diameter area) is adjusted in thickness to have a predetermined thickness depending on a setup value of the attenuation amount set to the corresponding transmissive unit 4. In consideration of variation in attenuation amount as described previously, this region is, however, configured to be thinner than a thickness capable of establishing the setup attenuation amount, in order to ensure its portion of 1 to 2% as a margin for adjustment by the adjustment sheet 2. Actually, in further consideration of material's own variation, when a thickness equivalent to the attenuation amount setup to the corresponding transmissive unit 4 is given as "1", the transmissive plate is adjusted to have an attenuation amount equivalent to less than "1", i.e. 0.93 to 0.98 (reduction rate of from 2 to 7%). For example, in the case where the attenuation amount of the energy is set as a water-equivalent thickness corresponding to an in-body mean range and the setup value is 64 mm, when a polyethylene block with a density of from 0.94 to 0.96 g/cm$^3$ is used, by adjusting its actual thickness to 64 mm, it is possible to prepare the transmissive plate 1 whose water-equivalent thickness is less than the water-equivalent thickness of 64 mm, leaving a margin for adjustment. Meanwhile, the adjustment sheet 2 is made to be superimposed, when said transmissive plate 1 is used in the irradiation device, over the transmissive plate 1 so that a predetermined water-equivalent thickness is attained. The thickness of the adjustment sheet 2 can be adjusted in such a manner of laminating a plurality of polyethylene sheets each being pre-adjusted in thickness or polyethylene sheets each being thinner than the margin for adjustment.

Note that, as the plurality of the respective transmissive units 4 are represented by 4-1 to 4-n, there are shown, in FIG. 1(a), the transmissive unit 4-1 staying at the retracted position and the unit 4-i staying at the irradiation position. Further, as shown in FIG. 1(b), the respective transmissive units 4 include those of typical three types that are different in structures of the transmissive plate 1 itself and the frame 3 holding the transmissive plate 3, depending on the thickness of each transmissive plate 1, which are indicated as Type-A, Type-B and Type-C, respectively. And, FIG. 1(b) shows cross-sectional views taken along line I-I in FIG. (a) for showing portions of the transmissive units 4 corresponding to the respective Type-A, Type-B and Type-C, in order to illustrate the three types of structures. Note that, in FIG. 1(b), although pan-head screws are shown for clarifying the screw positions, what is actually used are countersunk screws with their heads unprojected.

The structures of the transmissive units 4 will be described separately for a commonly-configured portion in the respective types and for a characterizing portion in each type.

<Common in Respective Types>

Each frame 3 has one end portion fixed to the driving cylinder 12 and the other end portion that serves as a holder portion for holding the transmissive plate 1 and the adjustment sheet 2. The portion that holds the transmissive plate 1 and the adjustment sheet 2 is opened so as not to shut the region where the particle beam goes in or goes out.

<Type-A>

The transmissive unit 4 of Type-A is to be applied to the transmissive plate 1 with a thickness of 4 mm or less, and its shape in overhead view corresponds to the transmissive unit 4-1 in FIG. 1(a). The frame 3 is configured with a fixed frame 31 in which its one end portion is fixed to the driving cylinder 12 and an opening is formed in the other end portion, and a clamping frame 32 having an opening similar to the above, for clamping in between it and the fixed frame 31, the transmissive plate 1 and the adjustment sheet 2 together. At corner portions of the clamping frame 32, loose holes for passing the screws 6 are formed, and at the positions on the fixed frame 31 corresponding to the holes, thread grooves for fastening the screws 6 are formed. The transmissive plate 1 is flatly shaped, in which holes are formed for passing the screws 6 for fastening the frame 3 and the adjustment sheet 2 together. Namely, although the relatively-thin transmissive plate 1 and the adjustment sheet 2 are held together by the frame 3, the adjustment sheet 2 is made attachable/releasable in the transmissive unit 4.

<Type-B>

The transmissive unit 4 of Type-B is to be applied to the transmissive plate 1 with a thickness in a range from 4 mm to 16 mm, and, like Type-A, its shape in overhead view corresponds to the transmissive unit 4-1 in FIG. 1(a). Also, the structure of the frame 3 is similar to that of Type-A. Meanwhile, with respect to the transmissive plate 1, in order to reduce its thickness as a whole, its fringe portion is cut down so as to be fitted partially in the opening of the fixed frame 31. Further, like Type-A, the transmissive plate 1 and the adjustment sheet 2 are held together by the frame 3, and the adjustment sheet 2 is made attachable/releasable in the transmissive unit 4.

<Type-C>

The transmissive unit 4 of Type-C is to be applied to the transmissive plate (block) 1 with a thickness more than 16 mm, and its shape in overhead view corresponds to the transmissive unit 4-*i* in FIG. 1(*a*). The frame 3 is configured with a fixed frame 31 in which its one end portion is fixed to the driving cylinder 12 and an opening is formed in the other end portion, an intermediate frame 33 fixed to the fixed frame 31 through a spacer 34 as being apart from the fixed frame 31 according to the thickness of the transmissive plate 1, and a clamping frame 32 for clamping in between it and the intermediate frame 33, the adjustment sheet 2.

At corner portions of the clamping frame 32, loose holes for passing the screws 6a are formed, and as corresponding to the positions of the holes, thread grooves for fastening the screws 6a are formed on the intermediate frame 33. At corner portions of the fixed frame 31, screw holes for fastening the screws 6c for fixing the transmissive plate 1 are formed. In addition, at middle portions of the respective sides of the intermediate frame 33, loose holes for passing the screws 6b are also formed; at the positions on the fixed frame 31 corresponding to that holes, thread grooves for fastening the screws 6b are formed; and on the clamping frame 32, incisions are formed so as not to interfere with the heads of the screws 6b.

With respect to the transmissive plate 1, in order to reduce the thickness as the transmissive unit 4, its fringe portion is cut down so as to be fitted partially in the opening of the fixed frame 31, and it is formed into a flange-like shape so as to be fixed to the fixed flame 31. Namely, the heavy transmissive plate 1 is solely held by the fixed frame 31, while the adjustment sheet 2 is held by the intermediate frame 33 and the clamping frame 32, independently of the transmissive plate 1. Thus, the adjustment sheet 2 is made attachable/releasable in the transmissive unit 4, independently of the heavy transmissive plate 1.

Namely, at least one of the frame 3 and the transmissive plate 1 serves as a superimposing mechanism that releasably superimposes the adjustment sheet 2 over the transmissive plate 1. Note that, shown in this embodiment is a case where the transmissive units 4 are configured with those of three types depending on the thickness of each transmissive plate 1; however, the types are not limited thereto, and may be more than or less than three. Further, the number of the transmissive units 4 (thickness types of the transmissive plate 1) is not required to be limited, and may be singular or plural; however, for example, if the transmissive plates 1 of a binary type each having a thickness t=0.5 to 64 mm are to be arranged, N number of types becomes necessary, where N (=8) satisfies $0.5 \times 2^{(N-1)} = 64$. Note that, for example, if the thickness of the transmissive plate 1 is adjusted to be a water-equivalent thickness that is less by R % than the setup value of the water-equivalent thickness, by adjusting the thickness of the adjustment sheet 2 within a thickness up to maximum two-fold of R %, it is possible to make adjustment to the setup value. Thus, its suffices that each frame 3 releasably holds the adjustment sheet having a thickness of up to 2R%.

Meanwhile, since the frame 3 releasably holds the adjustment sheet 2 by clamping its fringe portion, the number of sheets to be clamped has no limit. Thus, it is not necessary to configure by a single sheet, the adjustment sheet 2 for making adjustment to the required water-equivalent thickness. Therefore, the required water-equivalent thickness may be adjusted by a lamination of sheets each having an appropriate thickness. For that reason, the superimposing mechanism (frame 3 or the transmissive unit 4 including the same) is desired to be configured in such a manner that the adjustment sheet 2 is placed in the upper side of the transmissive plate 1 in a vertical direction of the range shifter 10 in a state of being installed, so as to make easier the replacement or the overlapping of the adjustment sheet 2.

Next, the irradiation device and the particle beam therapy system which are provided with the range shifter 10 according to Embodiment 1 of the invention, will be described using FIG. 2 and FIG. 3, As shown in FIG. 2, the irradiation device 100 includes a scanning electromagnet (for example, Wobbler Magnets) 20 that serves as an irradiation nozzle for enlarging the irradiation field by scanning a particle beam B supplied from a beam source; a scatterer 30 that is formed of lead or the like and scatters the particle beam B; a ridge filter 40 that is formed of aluminum or the like and spreads the width of the Bragg peak depending on the thickness of the irradiation target; the range shifter 10 as described above; a multi-leaf collimator 50 that is configured with a leaf portion comprising a plurality of leaf plates and a leaf movement mechanism for moving each of the leaf plates, and serves to make restriction so that the irradiation field (planar shape) matches the shape of the deceased site; and a range monitor 60 used for later-described adjustment of the adjustment sheet 2. Note that, in actual treatment, a bolus 120 is used that is fabricated for every patient K so as to be matched with a shape in depth of the deceased site (irradiation target), and makes restriction on a range distribution of the particle beam B.

As shown in FIG. 3, the particle beam therapy system includes, as a source of supplying the particle beam B, a circular accelerator 400 which is a cyclotron (hereinafter, referred to simply as "accelerator"); transport paths 300 for transporting the particle beam supplied from the accelerator 400 to, among a plurality of treatment rooms (200-1 to 200-*n*; referred to collectively as 200), a selected treatment room 200; and irradiation devices (100-1 to 100-*n*; referred to collectively as 100) each provided with the range shifter 10 as described above and placed in each treatment room 200, for irradiating the patient K with the particle beam B transported by the transport path 300.

The treatment room 200 is a room for performing a treatment by actually irradiating the patient K with the particle beam, and the irradiation device 100 is provided in each treatment room 200. Note that in the figure, there is shown a case where the treatment room 200-1 is a rotating irradiation room (called also as a rotary gantry) in which the irradiation device 100 is rotatable as a whole about the patient K (treatment table) to thereby freely set an irradiation angle of the particle beam to the patient K. Meanwhile, the treatment room 200-2 is shown as a horizontal irradiation room that irradiates the patient K fixed to a treatment table whose angle and position is freely settable, in a horizontal direction with the particle beam from the irradiation device 100-2. In such a manner, generally, to the single accelerator 400, a plurality of treatment rooms 200 including those of different types and/or the similar types, are connected through the transport paths 300.

Note that the transport path 300 is formed by joining vacuum ducts 310 each providing a transport cavity for the particle beam B, and is provided with a switching electromagnet 320 that is a switching device for switching the beam trajectory of the particle beam B toward the supply-destination treatment room 200, and with a deflection electromagnet 330 that deflects the particle beam B by a predetermined angle. Connection is established from a main-path 300-0 directly connected to the accelerator 400, to sub-paths 300-1 to 300-*n* corresponding to the respective treatment rooms 200, through the switching electromagnet 320. Namely, even if there are provided the irradiation devices 100 with specifications similar to each other, the particle beam B is supplied through the different transport path 300 for each of the treatment rooms 200.

Next, operations of the particle beam therapy system and the irradiation device will be described, Charged particles entered into the accelerator 400 are accelerated by a high-frequency electric field up to approx. 70 to 80% of the light velocity while being bent by the magnets, and are then emitted as the particle beam B into the transport path 300. In the transport path 300, the emitted particle beam B is led to the irradiation device 100 provided in the designated treatment room 200, by switching, if necessary, the transport path (300-1 to 300-$n$) by the switching electromagnet 320.

Although the particle beam B supplied to the irradiation device 100 is in a state of less than several millimeters in diameter i.e. a so-called pencil beam, it is caused to scan as if it draws, for example, a circle orbit by the scanning electromagnet 20, and then scattered by the scatterer 30, so that its irradiation field is enlarged in an extending direction of a plane (plane direction) perpendicular to the beam axis. The particle beam B with the irradiation field enlarged in the plane direction, passes through the ridge filter 40. The ridge filter 40 is formed, for example, of a number of cone-like objects or cross-sectionally triangle plates, that are arranged in the plane direction, so that there are portions of the particle beam B each passing through different thicknesses in each region divided in the plane direction. In the figure, for ease of understanding, it is illustrated as triangle poles arranged laterally. This makes the Bragg peak to be spread, so that the beam becomes to have an SOBP (Spread-Out Bragg Peak) with a predetermined width. That is, by means of the ridge filter 40, the irradiation field becomes spread also in the beam axis direction (depth direction).

Then, the particle beam B whose irradiation field has been spread, passes through the range shifter 10. In the range shifter 10, the energy (range) of the particle beam B is adjusted by placing a given transmissive unit 4 in the entrance region so as to cause the particle beam B to transmit through the transmissive plate 1 and the adjustment sheet 2 that are adjusted to provide an intended water-equivalent thickness (attenuation amount). Because the range is adjusted by the range shifter 10, it is possible to irradiate (to impart dose in) an intended in-body depth with the particle beam B.

Then, the particle beam B passes through the multi-leaf collimator 50. The multi-leaf collimator 50 forms an intended opening shape by positioning its plural sets of mutually facing plates at predetermined positions in a direction getting away from or getting close to the beam axis. Thus, the irradiation field of the particle beam B after passing through the multi-leaf collimator 50 is formed into a plane-direction shape matching the shape of the deceased site.

Finally, the particle beam B passes through the bolus 120. The bolus 120 is a limiter made of a resin or the like, and is formed into a configuration that compensates for a distal shape, for example, of the deceased site, as the depth-direction shape of the deceased shape. The distal shape means an uneven shape in the deepest side of the deceased site Here, the irradiation field is restricted in energy distribution in an extending direction of the plane (shaped in z-direction), so as to have a shape that is the same as the distal shape. That is, the depth direction shape of the irradiation field of the particle beam B is formed.

In the case of performing irradiation by a layer-stacking conformal irradiation method using the irradiation device 100 as described above, the dose injection is made such that spatially-imparted dose is given as being divided in the depth direction. At the initiation of irradiation, the scanning electromagnet 20, the range shifter 10 and the multi-leaf collimator 50 are set in conformity to the dose to be imparted to a layer (slice) including the deepest portion, and then the patient K is irradiated with the particle beam B. After completion of irradiation to the layer (slice) of the deepest portion, the range is adjusted by the range shifter 10 automatically in conformity to a position shallower (a near side viewed from irradiation source) by a depth corresponding to the width of the Bragg peak, and also, the settings of the scanning electromagnet 20 and the multi-leaf collimator 50 are changed, so that irradiation to the next layer is performed. Thereafter, while adjusting the range similarly by the range shifter 10, and changing the settings of the scanning electromagnet 20 and the multi-leaf collimator 50, an optimized dose is imparted as a whole to the shape of the deceased site.

In such a particle beam therapy system, the range shifter 10 have an important role in determining the position in each slice. Namely, unless otherwise the water-equivalent thickness (attenuation amount) set in the treatment plan is achieved by the range shifter 10, the irradiation field is shifted relative to the deceased site in the depth direction. Thus, not only a sufficient dose is not imparted to the deceases site, but also a surrounding normal tissue is damaged. Accordingly, for example, even if the setup pitch of the range shifter 10 is 1 mm in the treatment plan, it is required for the range shifter 10 to achieve a water-equivalent thickness accurately with a precision finer than the setup pitch.

Meanwhile, as described above, in the particle beam therapy system, a difference in transport path exists for each treatment room 200, in terms of the number of times passing the switching electromagnet 320, the defection electromagnet 330 and the like, and the path length of the vacuum ducts 310. Further, in the irradiation devices 100 in the respective treatment rooms 200, the specifications and the adjusted conditions of the scanning electromagnet 20, the scatterer 30 and the ridge filter 40 are not always the same. Namely, depending on the adjusted condition of the installed treatment room 200 or irradiation device 100, the particle beam B does not always pass through the range shifter 10 in the same condition.

Thus, as described in BACKGROUND ART, even if the range shifters 10 can be fabricated in the same specification, the attenuation amount changes depending on what the installed irradiation device 100 is, or changes even in the same irradiation device 100 if its condition has changed by the maintenance or the like. Thus, as described for the range shifter 10 according to Embodiment 1 of the invention, the transmissive plate 1 has been adjusted to have a thickness equivalent to the attenuation amount that is lower than the setup value of the attenuation amount, and the transmissive unit 4 is configured such that the adjustment sheet 2 can be superimposed releasably. This allows to make adjustment to a really-required attenuation amount by adjusting the thickness of the adjustment sheet 2.

This method of adjusting the attenuation amount will be described using a flowchart in FIG. 4. Here, description is made to the range shifter 10 having a plurality of transmissive units 4, and a water-equivalent thickness is used as the setup value of the attenuation amount for making its concept easily understandable.

First, the range monitor 60 (FIG. 1) is placed at an irradiation position of the particle beam B that is downstream of the range shifter 10 (Step S10). Then, the range shifter 10 is driven so that the transmissive unit 4 subject to adjustment is placed at an irradiation position (Step S20). Subsequently, the range shifter 10 is irradiated with the particle beam B (Step S30), and its range is measured by the range monitor 60 in the downstream side (Step S40).

Then, it is determined whether or not the measured range falls within a value acquired from the water-equivalent thickness required for that transmissive unit 4 (Step S50). If not within the value (Step S50, "N"), a thickness adjustment is performed by adjusting the thickness, the number, or its combination, of a sheet(s) used as the adjustment sheet 2 (Step S200), and then the flow moves to Step S30. On the other side, if within the value (Step S50,"Y"), it is determined whether the adjustment is completed or not (Step S60). If there remains another transmissive unit 4 to be adjusted and thus the adjustment is not completed (Step S60,"N"), the flow moves to Step S20. In contrast, if all of the transmissive units 4 have been adjusted and thus the adjustment is completed (Step S60, "Y"), the range monitor 60 is retracted (Step S70) and the adjustment is ended.

In the particle beam therapy system after the above adjustment, even if an actual treatment is performed in any treatment room 200 among the treatment rooms 200 and among treatment rooms 200 that are at least subjected to the adjustment, it is possible to make adjustment to a constant and ideal water-equivalent width, so that the treatment can be performed while ensuring compatibility with the treatment plan.

For example, if such an adjustment is performed for every maintenance such as a periodic inspection so as to adjust the water-equivalent width of the range shifter 10, even when only a given treatment room 200 is subjected to the maintenance, it is possible to hold a compatibility with another treatment room, and even when the treatment room 200 is changed, it is possible to hold a compatibility with the treatment plan.

Note that materials of the transmissive plate 1 and the adjustment sheet 2 are also not limited to the above-described materials so far as they are materials having resistance to radiation and not causing unnecessary scattering, and may be acrylic or polyimide materials, for example.

As described above, the range shifter 10 according to Embodiment 1 is a range shifter 10 that outputs the particle beam B incident thereto while attenuating energy of the particle beam B, which comprises: the transmissive plate 1 whose thickness has been adjusted according to a setup value (for example, a water-equivalent thickness) of an amount of the energy to be attenuated; and the frame 3 serving as a holder portion that holds the transmissive plate 1; wherein the thickness of the transmissive plate 1 is adjusted to be a thickness equivalent to an attenuation amount lower than the setup value by a predetermined rate thereof; and wherein the superimposing mechanism capable of releasably superimposing the adjustment sheet 2 over the transmissive plate 1, is provided to at least one of the transmissive plate 1 and the holder portion 3, said adjustment sheet 2 being adjusted to have a thickness equal to or less than a thickness equivalent to a two-fold attenuation amount of the predetermined rate. Thus, even when the attenuation amount of the energy changes due to a change in the condition of the incident particle beam B caused by a difference between the installed irradiation devices 100 or by the maintenance, it is possible to make adjustment to the setup attenuation amount of the energy by superimposing the adjustment sheet 2 whose thickness can be adjusted. Thus, it is possible to output the particle beam B while adjusting its range accurately.

In particular, when the predetermined rate used for making lower than the setup value is set to from 2 to 7%, it is possible to make adjustment to the intended water-equivalent thickness by adjusting the thickness of the adjustment sheet 2, even if the condition of the incident particle beam B has changed to the maximum extent.

When at least one of the frame 3 and the transmissive plate 1 that constitutes the superimposing mechanism, is configured to superimpose the adjustment sheet 2 over the transmissive plate 1 in the incident side of the particle beam, in a case of irradiation device 100 that makes irradiation with the particle beam in a vertical direction, the adjustment sheet 2 is placed in the upper side of the transmissive plate 1 in a vertical direction of the range shifter 10 in a state of being installed. Thus, it is possible to easily adjust the thickness of the adjustment sheet 2 by its replacement.

Meanwhile, the particle beam therapy system according to Embodiment 1 comprises: the accelerator 400 that generates the particle beam B; the plurality of treatment rooms 200; the transport paths 300 that connect between the accelerator 400 and each of the plurality of treatment rooms 200; and the irradiation device 100 provided in each of the plurality of treatment rooms 200, that forms the particle beam B supplied through the transport path 300 into an irradiation field that matches an irradiation target, to thereby irradiate the irradiation target with the particle beam B; wherein the above-described range shifter 10 is provided in the irradiation device 100. Thus, even if any one of the treatment rooms 200 is used, it is possible to make irradiation with an accurate and compatible irradiation field.

DESCRIPTION OF REFERENCE NUMERALS AND SIGNS

1: transmissive plate, 2 adjustment sheet, 3: frame, 4: transmissive unit, 10: range shifter, 11: housing, 12: cylinder, 20: scanning electromagnet, 30: scatterer, 40: ridge filter, 50: multi-leaf collimator, 60: range monitor, 100: irradiation device, 200: treatment room, 300: transport path, 400: accelerator.

The invention claimed is:

1. A range shifter that outputs a particle beam incident thereto while attenuating energy of the particle beam, comprising:
    a transmissive plate whose thickness has been adjusted based on a setup value of an amount of the energy to be attenuated; and
    a holder portion that holds the transmissive plate;
    wherein the thickness of the transmissive plate is adjusted to a thickness equivalent to an attenuation amount that is lower than the setup value by a predetermined rate; and
    wherein at least one of the transmissive plate and the holder portion is provided with a superimposing mechanism configured to releasably superimpose an adjustment sheet over the transmissive plate, said adjustment sheet being adjusted such that it has a thickness equal to or less than twice the attenuation amount of the predetermined rate.

2. The range shifter of claim 1, wherein the predetermined rate is set to from 2% to 7%.

3. The range shifter of claim 2, wherein the superimposing mechanism superimposes the adjustment sheet over the transmissive plate on the incident side of the particle beam.

4. A particle beam therapy system comprising:
    an accelerator that generates a particle beam;
    a plurality of treatment rooms;
    transport paths that connect between the accelerator and each of the plurality of treatment rooms; and
    an irradiation device provided in each of the plurality of treatment rooms, that forms the particle beam supplied through the transport path into an irradiation field that matches an irradiation target, to thereby irradiate the irradiation target with the particle beam,
    wherein the range shifter of claim 3 is provided in the irradiation device.

5. A particle beam therapy system comprising:
    an accelerator that generates a particle beam;
    a plurality of treatment rooms;

transport paths that connect between the accelerator and each of the plurality of treatment rooms; and an irradiation device provided in each of the plurality of treatment rooms, that forms the particle beam supplied through the transport path into an irradiation field that matches an irradiation target, to thereby irradiate the irradiation target with the particle beam, wherein the range shifter of claim 2 is provided in the irradiation device.

6. The range shifter of claim 1, wherein the superimposing mechanism superimposes the adjustment sheet over the transmissive plate on the incident side of the particle beam.

7. A particle beam therapy system comprising:

an accelerator that generates a particle beam;

a plurality of treatment rooms;

transport paths that connect between the accelerator and each of the plurality of treatment rooms; and an irradiation device provided in each of the plurality of treatment rooms, that forms the particle beam supplied through the transport path into an irradiation field that matches an irradiation target, to thereby irradiate the irradiation target with the particle beam, wherein the range shifter of claim 3 is provided in the irradiation device.

8. A particle beam therapy system comprising:

an accelerator that generates a particle beam;

a plurality of treatment rooms;

transport paths that connect between the accelerator and each of the plurality of treatment rooms; and an irradiation device provided in each of the plurality of treatment rooms, that forms the particle beam supplied through the transport path into an irradiation field that matches an irradiation target, to thereby irradiate the irradiation target with the particle beam, wherein the range shifter of claim 1 is provided in the irradiation device.

\* \* \* \* \*